US006682920B1

(12) United States Patent
Stephens et al.

(10) Patent No.: US 6,682,920 B1
(45) Date of Patent: Jan. 27, 2004

(54) COMPOSITIONS AND METHODS FOR IDENTIFYING PKB KINASE INHIBITORS

(75) Inventors: Len Stephens, Cambridge (GB); Philip Hawkins, Cambridge (GB); David Stokoe, San Francisco, CA (US)

(73) Assignee: Onyx Pharmaceuticals, Inc., Richmond, CA (US)

(*) Notice: Subject to any disclaimer, the term of this patent is extended or adjusted under 35 U.S.C. 154(b) by 0 days.

(21) Appl. No.: 09/156,793

(22) Filed: Sep. 17, 1998

Related U.S. Application Data

(60) Provisional application No. 60/060,190, filed on Sep. 26, 1997.

(51) Int. Cl.[7] .................... C12N 9/12; C12N 15/54; C12N 15/79; C12Q 1/48
(52) U.S. Cl. ............... 435/194; 435/69.1; 435/252.3; 435/320.1; 435/15; 536/23.2
(58) Field of Search .................. 435/15, 69.1, 194, 435/252.3, 320.1; 536/23.2

(56) References Cited

U.S. PATENT DOCUMENTS

| | | | |
|---|---|---|---|
| 5,593,833 A | * 1/1997 | Morison et al. | 435/6 |
| 5,962,232 A | * 10/1999 | Bandman et al. | 435/6 |
| 5,981,176 A | * 11/1999 | Wallace | 435/6 |

FOREIGN PATENT DOCUMENTS

| | | | |
|---|---|---|---|
| WO | WO 97/22360 | | 6/1997 |
| WO | WO 98/41638 | * | 9/1998 |

OTHER PUBLICATIONS

Frech, M., et al., 1997, The Journal of Biological Chemistry, vol. 272, "High affinity binding of inositol phosphates and phosphoinositides to the pleckstrin homology domain of RAC/protein kinase B and their influence on kinase activity", pp. 8574–8481.*

Shaw, M., et al., 1997, FEBS Letters, vol. 416, "Further evidence that the inhibition of glycogen synthase kinase 3beta is mediated by PDK1/PKB–induced phosphorylation of Ser–9 and not by dephosphorylation of Tyr–216", pp. 307–311.*

Alessi D.R. et al. "Characterization of a 3–phosphoinositide–dependent ... " Current Biology, V. 7, No. 4, Mar. 1997, pp. 261–269.

Alessi D.R. et al. "3–phosphoinositide–dependent protein kinase–1 (PDK1) ... " Current Biology, V. 7, No. 10, Sep. 1997, pp. 776–789.

Stokoe et al., "Dual role of phosphatidyl–3,4,5–triphosphate in the ... " Science, V. 277, Jul. 1997, pp. 567–570.

P. Cohen et al., "PDK1, one of the missing links in insulin signal transduction?" FEBS Letters, V. 410, No. 1, Jun. 1997, pp. 3–10/.

L. Stephens et al., "Protein kinase B kinases that mediate phosphatidylinositol ... " Science, V. 279, Jan. 1998, pp. 710–714.

* cited by examiner

Primary Examiner—Ponnathapu Achutamurthy
Assistant Examiner—William W. Moore
(74) Attorney, Agent, or Firm—Gregory Giotta

(57) ABSTRACT

Compositions and methods are described that are useful to assay for compouds that affect PKB kinase activity which have medical applications for the diagnosis and treatment of disease.

13 Claims, 9 Drawing Sheets

```
            ADADALQHTAQPPQPR               ILGEGSFSTVVLAR
  1  MDGTAAEPRPGAGSLQHAQPPPQPRKKRPEDFKFGKILGEGSFSTVVLARELATSREYAI

61  KILEKRHIIKENKVPYVTRERDVMSRLDHPFFVKLYFTFQDDEKLYFGLSYAKNGELLKY

121  IRKIGSFDETCTRFYTAEIVSALEYLHGKGIIHRDLKPENILLNEDMHIQITDFGTAKVL

ANHFVGTAQYVSPELLTER
181  SPESKQARANSFVGTAQYVSPELLTEKSACKSSDLWALGCIIYQLVAGLPPFRAGNEYLI

241  FQKIIKLEYDFPEKFFPKARDLVEKLLVLDATKRLGCEEMEGYGPLKAHPFFESVTWENL

301  HQQTPPKLTAYLPAMSEDDEDCYGNYDNLLSQFGCMQVSSSSSHSLSASDTGLPQRSGS

361  NIEQYIHDLDSNSFELDLQFSEDEKRLLLEKQAGGNPWHQFVENNLILKMGPVDKRKGLF

QLLLTEGPHLYYVDPVNK
421  ARRRQLLLTHGPHLYYVDPVNKVLKGEIPWSQELRPEAKNFKTFFVHTPNRTYYLMDPSG

481  NAHKWCRKIQEVWRQRYQSHPDAAVQ
```

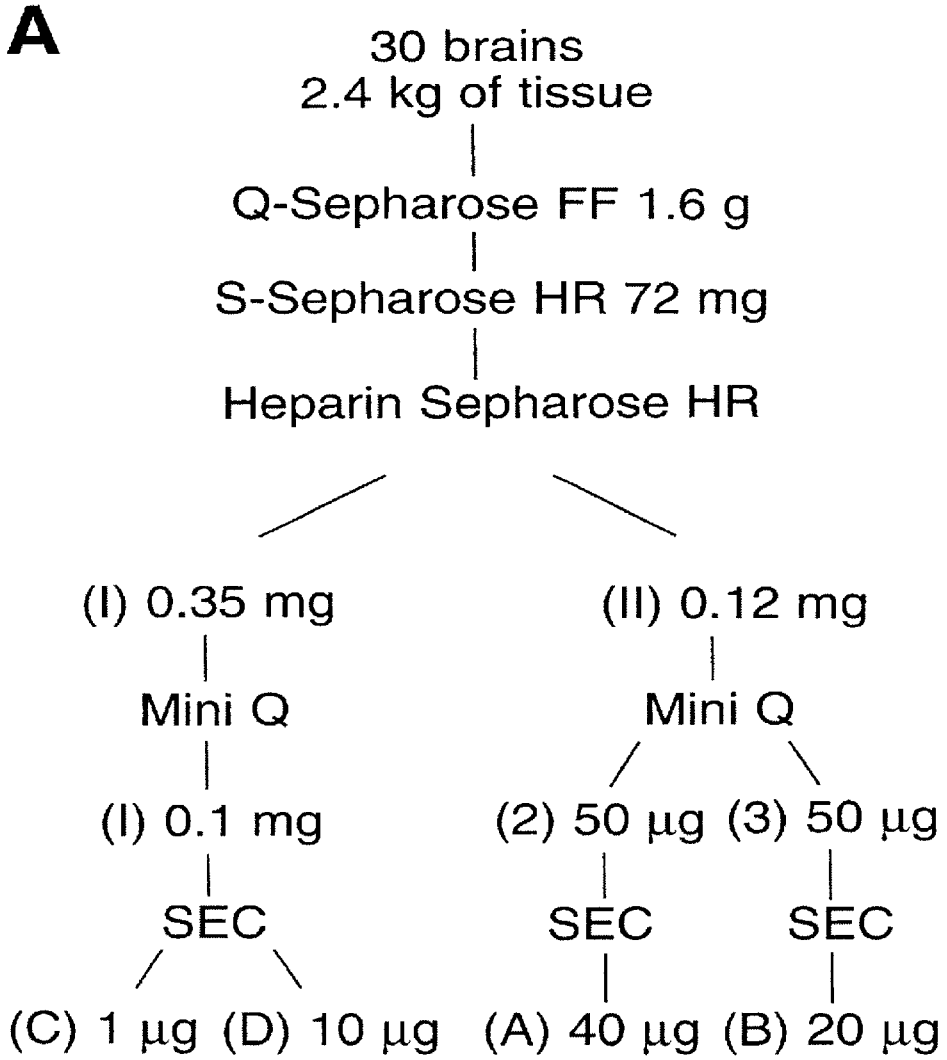

Phosphorylation and activation of PKB

Phosphorylation of PKB by PKB Kinase A

Association of PKB with lipid vesicles

```
                ADADALQHTAQPPQPR              ILGEGSFSTVVLAR
  1   MDGTAAEPRPGAGSLQHAQPPPQPRKKRPEDFKFGKILGEGSFSTVVLARELATSREYAI

61   KILEKRHIIKENKVPYVTREROVMSRLDHPFFVKLYFTFQDDEKLYFGLSYAKNGELLKY

121   IRKIGSFDETCTRFYTAEIVSALEYLHGKGIIHRDLKPENILLNEDMHIQITDFGTAKVL

ANHFVGTAQYVSPELLTER
181   SPESKQARANSFVGTAQYVSPELLTEKSACKSSDLWALGCIIYQLVAGLPPFRAGNEYLI

241   FQKIIKLEYDFPEKFFPKARDLVEKLLVLDATKRLGCEEMEGYGPLKAHPFFESVTWENL

301   HQQTPPKLTAYLPAMSEDDEDCYGNYDNLLSQFGCMQVSSSSSSHSLSASDTGLPQRSGS

361   NIEQYIHDLDSNSFELDLQFSEDEKRLLLEKQAGGNPWHQFVENNLILKMGPVDKRKGLF

QLLLTEGPHLYYVDPVNK
421   ARRRQLLLTHGPHLYYVDPVNKVLKGEIPWSQELRPEAKNFKTFFVHTPNRTYYLMDPSG

481   NAHKWCRKIQEVWRQRYQSHPDAAVQ
```

COMPOSITIONS AND METHODS FOR IDENTIFYING PKB KINASE INHIBITORS

This application claims priority to U.S. Provisional patent application No. 60/060,190, filed Sep. 26, 1997.

FIELD OF THE INVENTION

This invention is in the field of molecular biology and involves the identification of protein kinase B kinases, and their medical applications.

BACKGROUND OF THE INVENTION

Insulin, and other growth factors, trigger the activation of phosphatidylinositol (PI) 3-kinase, the enzyme which converts PI 4,5 bisphosphate (PIP2) to the putative second messenger PI 3,4,5 trisphosphate (PIP3). There are multiple forms of PI 3-kinase, and they arc all able to phosphorylate the D-3 position of phosphatidylinositol (PtdIns), phosphatidylinositol-4-phosphate (PtdIns4-P) and phosphatidylinositol4,5-bisphosphate (PtdIns4,5-P2) to produce phosphatidylinositol-3-phosphate (PtdIns-3-P), phosphatidylinositol-3,4-bisphosphate (PtdIns-3,4-P2) and phosphatidylinositol-3,4,5-triphosphate (PtdIns-3,4,5-P3, or PIP3), respectively.

Protein kinase B (PKB) is in the signal transduction pathway of PIP3, and lies downstream of PI 3-kinase. See, Franke et al., (1995) Cell, vol. 81, pages 727–736. For example, activation of PKB by insulin or growth factors is prevented if the cells are preincubated with inhibitors of PI 3-kinase, the best known being Wortmannin or LY 294002, or by overexpression of a dominant negative mutant of PI 3-kinase. See, Burgering, B M. and Coffer, P. J. (1995) Nature, vol. 376, pages 599–602. Further, mutation of the tyrosine residues in the PDGF receptor that when phosphorylated bind to PI 3-kinase also prevent the activation of PKBα, an isoform of PKB. Recent reports have shown the PKB is itself activated by another kinase also downstream of PIP3. See, Alessi, D. R. et al., Curr. Biol. vol. 7, 261 (1997). This kinase, termed PKB kinase, or phosphatidylinositide (PtdIns) 3-kinase (PDK1), requires PIP3 for activation. See, Stokoe, D., et al (1997) Science, vol. 277, pages 567–570.

PKB is a key enzyme in the PIP3 pathway, and is involved in regulating cell growth. It has been implicated in certain human cancers; for instance, it is known to be amplified in a percentage of ovarian carcinomas, breast carcinomas, and pancreatic carcinomas. See, Bellacosa, A. et al. (1995) Int. J. Cancer 64, pages 280–285, and Cheng, J. Q. et al. (1996) Proc. Natl. Acad. Sci. U.S.A. vol. 93, 3636–3641. The amplification of the enzyme affords tumor cells a mechanism to circumvent apoptosis. Thus, it will be appreciated that drugs that inhibit PKB activity will be beneficial for the treatment of diseases involving unwanted cell growth, including cancer. One way to achieve this end is to develop assays that identify, such.

SUMMARY OF THE INVENTION

A first object of the invention is a description of PKB kinases, methods and compositions for purifying and expressing the kinases, and cDNA sequences that encode them.

A second object of the invention is a description of the activation of PKB kinases by PtdIns (3,4,5)P$_3$ to effect the phosphorylation of PKB.

A third object of the invention is a description of compositions and methods for identifying compounds that have prophylatic or therapeutic benefit for treating diseases involving unwanted cell growth, including cancer.

These and other objects of the invention will become apparent to a skilled practitioner of this art upon a full disclosure of the invention.

Figure 1B:
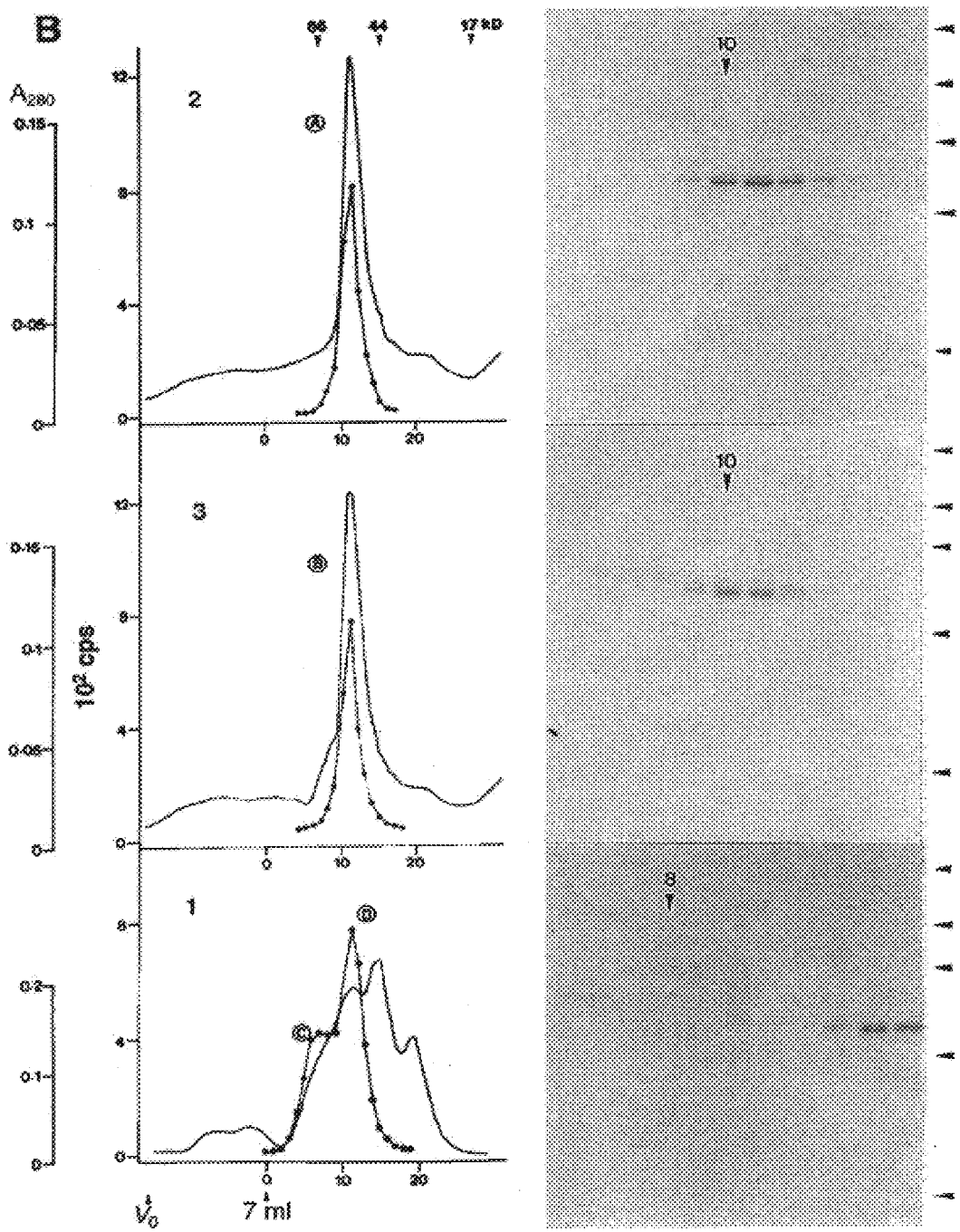
FIG. 1. Purification of PKB kinases from sheep brain A. The flow diagram summarizes the purification of PKB kinases A–D from sheep brain cytosol and records the quantity of protein carried through each step. The overall recovery of activity from the initial cytosol fractions was 15.5%.

B. The figure shows the Abs 280 nm, PKB kinase activity, profiles and Coomassie-stained SDS-PAGE gels, analyzing the elution of proteins from the final columns, all HPLC size-exclusion columns (SEC) in the purification of PKB kinases A–D. HPLC-SEC was performed with a Biosilect column (VT 11.6 mls, BioRad). 35–45 ul samples were loaded, the flow was 40 ul/min, 80 ul fractions were collected. The SEC buffer contained 0.15 M NaCl, 20 mM HEPES pH 7.4, 40 C, 0.5 mM EGTA 0.1 mM EDTA, 1% betaine, 0.03% Tween 20, 0.01% azide, 2 mM B-glycerophosphate, 1 mM DTT and pepstatin A, leupeptin, aprotinin and antipain, all at 2 ug/ml.

The native sizes of the PKB kinases A–D were estimated to be 58, 58, 68 and 54 kD, respectively, and their SDS-denatured sizes to be 57, 57, 70 and 55 kD respectively (the position to which 220, 97, 69, 46 and 31 kD standard had migrated during SDS-PAGE are indicated).

C. PKB kinase activity co-purifies with a [$^{32}$P]-PtdIns(3,4,5)P$_3$ binding protein. A partially purified preparation of PKB kinase was subjected to SEC and fractions were analyzed for PtdIns(3,4,5)P$_3$-dependent PKB kinase activity (bottom panel), [$^{32}$P] PtdIns(3,4,5)P$_3$ binding proteins (middle-panel, by probing a renatured. Western blot with [$^{32}$P]-PtdIns(3,4,5)P$_3$ (18)) and (C) SDS-denatured proteins (upper panel, by silver staining an SDS-PAGE gel).

[$^{32}$P]-PtdIns(3,4,5)P$_3$ binding was assayed by Western blotting proteins (samples only heated to 50° C. with SDS sample buffer) onto Nitrocellulose. The filter was incubated in PBS containing, 1% NP40, 1 mM EGTA, 0.01% azide, for 12 hrs at 4° C. The filter was blocked for 30 mins (room temperature) in the above solution additionally containing 0.1% cholate, 50 $\mu$gml$^{-1}$ phosphatidylserine and phosphatidylcholine, 1 mM MgCl$_2$ and 1 mM DTT. [$^{32}$P]-PtdIns(3,4,5)P$_3$ (prepared from recombinant p101/p120-PI3K, PtdIns(4,5)P$_2$ and [$\gamma^{32}$P]-ATP (See, L. R. Stephens et al, Cell 89, 105–114 (1997)) was sonicated into the block solution (10 $\mu$Ci in 10 mls) and applied to a blocked filter for 20 mins (room temperature) then washed away with fresh block solution (5× over 5 mins) and finally PBS containing 1% NP40. The filter was air dried and autoradiographed.

Figure 2A:
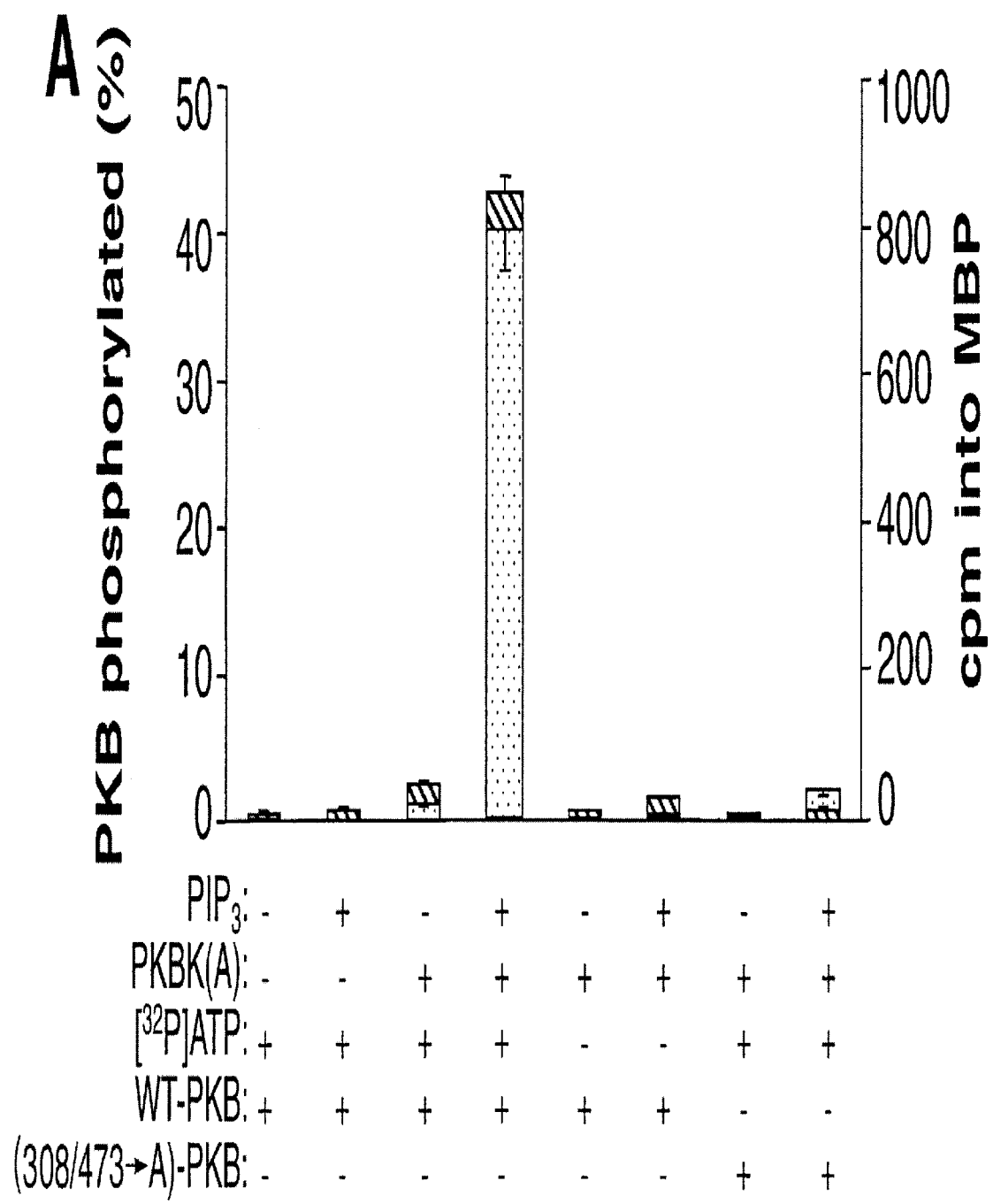

FIG. 2. Characterization of PKB kinases A–C.

A. The purified PKB kinases are PtdIns(3,4,5)P$_3$-dependent and activate PKB.

Assays were run in 2 stages. The first stage was run with mixed lipid vesicles either with or without D-D-S/A-PtdIns (3,4,5)P$_3$ (final concentration 5 $\mu$M) and in the presence or absence of PKB kinase A (6 nM), wild-type (EE)-PKB (2.5 $\mu$M) or T308A/S473A-(EE)-PKB) and [$\gamma^{32}$P]-ATP (50 $\mu$M). The assays were stopped and PKB proteins were immunoprecipitated with α(EE)-beads, washed then incubated with [$\gamma^{32}$P]-ATP (10 $\mu$M) and myelin basic protein (MBP; 7 $\mu$M) to determine the activity of the immobilized PKB. The results are from a single experiment and are represented as means±SE(n=3–5); four further experiments gave similar results. PKB kinases B, C and D gave very similar results.

B. Phospholipid specificity of activation of PKB phosphorylation.

Assays contained; a constant concentration of mixed lipid vesicles containing the indicated concentrations of inositol phospholipids, (EE)-PKB (2.5 µM), PKB kinase A (5 nM) and [$\gamma^{32}$P]-ATP (1 µM, total volume 12 µl). The data shown are pooled from 12 separate experiments and are means (n=3–6, their average se was 6%). Identical patterns of activation were observed for PKB kinases B, C and D.

To assay association of PKB and PKB kinases with lipid vesicles and the effects of different lipids on the phosphorylation of PKB, the lipid vesicles were prepared by: sonicating dry lipid films into 0.2 M sucose; 20 mM KCl; 20 mM HEPES, pH 7.4 30° C.; 0.01% azide (to give 200 µM phosphatidylcholine, 150 µM phosphatidylserine, 20 µM phosphatidylethanolamine, 10 µM spingomylin plus the indicated concentrations of inositol lipids final in the assay. These were mixed with the relevant kinases in an assay buffer containing 1 mgml$^{-1}$ BSA; 0.12 M NaCl; 1 mM EGTA; 0.2 mM calcium; 1.5 mM MgCl$_2$; 1 mM DTT; 0.01% azide; 5 mM KCl; 20 mM HEPES, pH 7.4, 30° C. (approx. 50 nM free calcium, all final concentrations in assay) with or without [$\gamma^{32}$P]-ATP (1 µM final concentration) and (EE)-PKB (2.5 µM final concentration). If the assays were to estimate associated of the kinases with the lipid vesicles then after 4 mins at 30° C. the assays were centrifuged (airfuge (Beckman) maximum speed for 30 mins). Aliquots of the supernatents were removed for assays or immunoblotting. The pellets were rinsed rapidly with assay buffer, recentrifuged and dissolved in SDS-sample buffer. Phosphorylation of PKB(s) were quantitated as described above.

C. Association of PKB with lipid vesicles.

(EE)-PKB (40 nM) was incubated with sucrose-loaded lipid vesicles (or their vehicle) under conditions similar to those in part B above. After 4 mins the vesicles were pelted by centrifugation and the quantities of PKB in the supernatents and pellets were quantitated by immunoblotting with an α-(EE) monoclonal antibody. The inset immunoblots show the results of an experiment with D-D-S/A-PtdIns(3,4,5)P$_3$ (maximum concentration in assay of 16 µM. See, A. Toker, L. C. Cantley, *Nature* 386, 673–67642 (1997))). The data shown are pooled from a total of 7 independent experiments and represent means (n=2–3, the average range about those means was 11.0%).

Figure 2B:
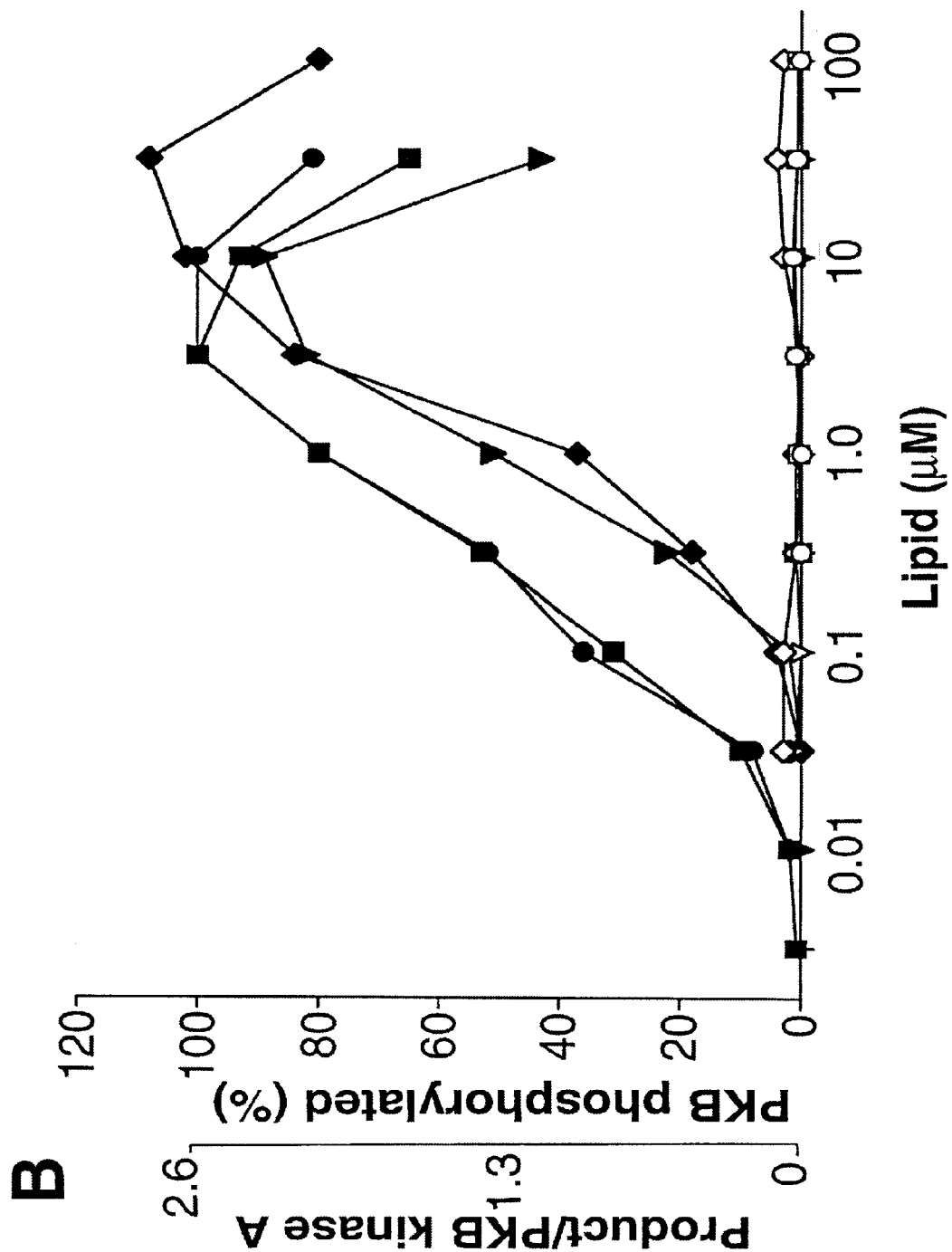

PBK kinase A (5 nM) was mixed with sucrose-loaded lipid vesicles (or their vehicle alone) containing various concentrations of inositol phospholipids as shown in FIG. 2B. After 4 mins and 30° C. the vesicles were pelted by centrifugation and aliquots of the supernatents were assayed of PKB kinase activity in the presence of 5 µM D-D-S/A-PtdIns(3,4,5)P$_3$. A mean of 8.2% of the total activity was sedimented in the presence of lipid vesicles containing no added inositol phospholipids, the activity remaining in the supernatent after centrifugation of lipid vesicles containing no added inositol lipids defined the 100% value to which other treatments were referred. The data WERE means (n=4–6, pooled from 16 separate experiments, the average SE was 8%).

FIG. 3. Primary structure of a PKB kinase

A minimum potential ORF defined by cDNAs isolated from our human U937 cell library is shown. The four peptide sequences derived from sheep brain PKB kinase A are shown in bold above the sequence. The are of homology to other protein kinase catalytic domains is boxed in a solid line the area of hololgy to other PH-domains is boxed in a dashed line.

Figure 4:
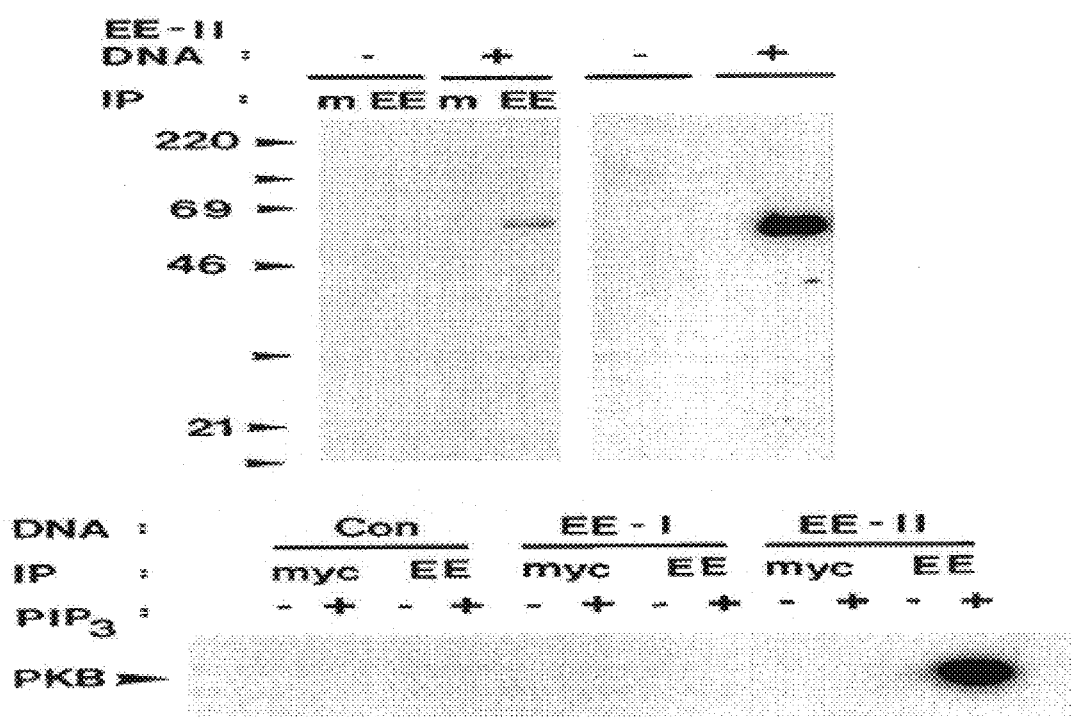

FIG. 4. Expression of PKB kinases in cos-7 cells

Mammalian expression vectors containing NH$_2$-terminal tagged versions of the PKB kinase open reading frame shown in FIG. 3. ((EE)-II refers to the complete ORF and (EE)-I refers to the 'kinase-compromised' splice variant) were transiently expressed in cos-7 cells. Proteins were purified via their (EE)-tags (myc antibodies were used as controls) and aliquots were Western blotted. PVDF filters, probed with an α(EE) monoclonal antibody (detection by ECL; right hand upper panel) were then stained with Coomassie blue (left hand upper panel; data shown are for (EE)-II only; similar results were obtained with (EE)-I). Aliquots were assayed for PKB kinase activity in the presence of lipid vesicles either with or without D-D-S/A-PtdIns (3,4,5)P$_3$ and [$\gamma^{32}$P]-ATP (300 nM; 3 µM and 1 µM final concentrations respectively). A photograph of an autoradiogram is shown displaying [$^{32}$P] in PKB.

Figure 5:
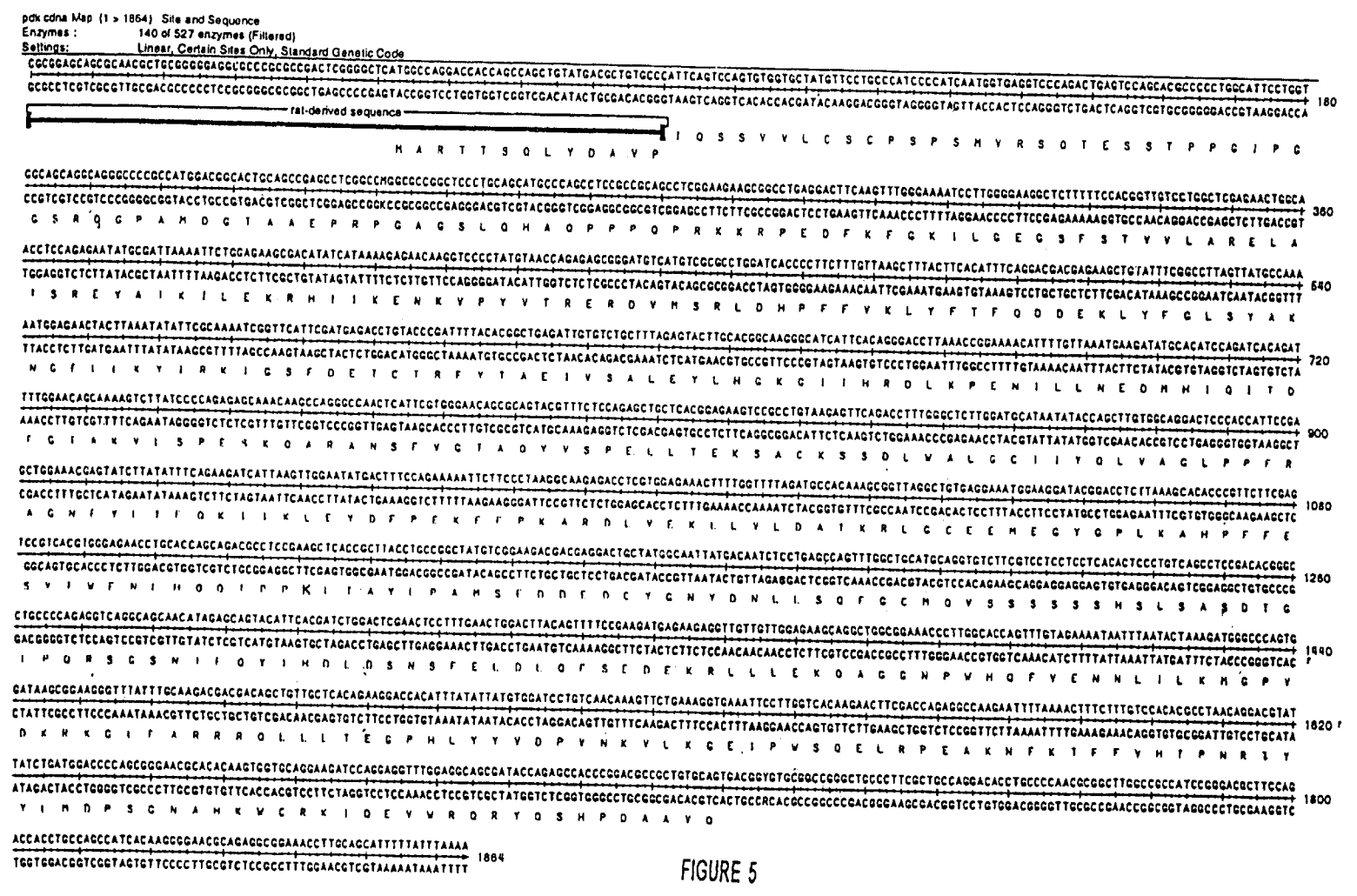

FIG. 5 shows a cDNA (Seq I. D. No. 1) and encoded amino acid sequence of a PKB kinase.

DETAILED DESCRIPTION OF THE INVENTION

All publications and patent applications mentioned in this specification are herein incorporated by reference to the same extent as if each individual publication or patent application was specifically and individually indicated to be incorporated by reference.

Definitions

At the outset it is worth noting that unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see generally, Sambrook et al., *Molecular Cloning: A Laboratory Manual, 2nd. edition* (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

PKB, or protein kinase B. is used herein to mean an approximately 60 kD kinase with homology to protein kinase c and protein kinase a, as described by Coffer, P. J. and Woodgett, J. R. (1991) Eur. J. Biochem. vol. 201, pages 475–481, and Jones, P. F. et al., (1991) Proc. Natl. Acad. Sci. USA vol. 88, 41714175. See also, WO 97/22360, and Stokoe, D., et al (1997) Science, vol. 277, pages 567–570. The definition includes isoforms of the enzyme of which four are presently known. PKB is also termed c-Akt or Rac-Pk.

The formal name of the 'biological stereoisomer isomer' of phosphatidylinositol(3,4,5)-trisphosphate is (for a specific fatty acid combination); (1-stearoyl, 2-arachidonyl) snphosphatidyl D-myo-inositol (3,4,5)-trisphosphate. We have abbreviated this, whilst retaining all of the relevant discriminatory precision to define specific isomers, to D-D-S/A-PtdIns(3,4,5)$P_3$; with the second D referring to the chirality of the glycerol back-bone i.e. D-L-S/A-PtdIns(3,4,5)$P_3$ is (2-arachidonyl, 3-stearoyl) sn-phosphatidyl D-myoinositol (3,4,5)-trisphosphate. Dipalmitoyl derivatives are abbreviated to D-D-P/P-PtdIns(3,4,5)$P_3$. The enantiomer of D-D-S/A-PtdIns(3,4,5)$P_3$ is L-L-S/A-PtdIns(3,4,5)$P_3$.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired.

The term "sequence homology" referred to herein describes the proportion of base matches between two nucleic acid sequences or the proportion amino acid matches between two amino acid sequences. When sequence homology is expressed as a percentage, e.g., 50%, the percentage denotes the proportion of matches over the length of sequence from a PKB kinase that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments the sequence homology between the target nucleic acid and the oligonucleotide sequence is generally not less than 17 target base matches out of 20 Possible oligonucleotide base pair matches (85%); preferably not less than 9 matches out of 10 possible base pair matches (90%), and most preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Chemistry terms herein are used according to conventional usage in the art, as exemplified by The McGraw-Hill Dictionary of Chemical Terms (ed. Parker, S., 1985), McGraw-Hill, San Francisco, incorporated herein by reference.

The production of proteins from cloned genes by genetic engineering is well known. See, e.g. U.S. Pat. No. 4,761,371 to Bell et al. at column 6, line 3 to column 9, line 65. (The disclosure of all patent references cited herein is to be incorporated herein by reference.) The discussion which follows is accordingly intended as an overview of this field, and is not intended to reflect the full state of the art.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading frame.

Suitable host cells include prokaryotes, yeast cells, or higher eukaryotic cells. Prokaryotes include gram negative or gram positive organisms, for example *Escherichia coli* (*E. coli*) or Bacilli. Higher eukaryotic cells include established cell lines (i.e. cos cells) of mammalian origin as described below. Exemplary host cells are DH5a *E. coli* W3110 (ATCC 27,325), *E. coli* B, *E. coli* X1776 (ATCC 31,537) and *E. coli* 294 (ATCC 31,446). Pseudomonas species, Bacillus species, and Serratia marcesans are also suitable.

In an insect system, *Autoyrapha californica* nuclear polyhidrosis virus (AcNPV) may be used as a vector to express foreign genes. (E.g., see Smith et al., 1983, J. Virol. 46: 584; Smith. U.S. Pat. No. 4,215,051). In one embodiment described below, Sf9 insect cells are infected with a baculovirus vectors expressing a PKB kinase construct with either a 6× histidine tag, myc, or an EE-tag (i.e. Glu-Glu-tag). "E" refers to the amino acid glutamine.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells. Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nucleic Acids Res.* 8, 4057 (1980) and EPO Application Publication Number 36,776) and the tac promoter (H. De Boeretal., *Proc. Natl. Acad. Sci. USA* 80, 21 (1983)).

Identification of PKB Kinases

PKB Kinases can be identified using several different techniques, including methods for detecting protein-protein interactions. At some point in the verification of PKB kinase activity it is expected that its activation by PIP3 will be determined. See, Stokoe, D., et al (1997) *Science*, vol. 277, pages 567–570.

Among the traditional methods which may be employed are co-immunoprecipitation, crosslinking and co-purification through gradients or chromatographic columns of cell lysates or proteins obtained from cell lysates, and to identify proteins in the lysate that phosphorylate target proteins, preferably PKB, or other suitable substrates. Such assays may employ full length PKB targets or a peptide. Once isolated, such an intracellular PKB Kinase can be identified, in turn, be used, in conjunction with standard techniques, to identify other proteins with which it interacts. For example, at least a portion of an amino acid sequence of an intracellular PKB Kinase which interacts with PKB can be ascertained using techniques well known to those of skill in the art, such as the Edman degradation technique. (See, e.g., Creighton, 1983, "Proteins: Structures and Molecular Principles", W.H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra., and PR Protocols: A Guide to Methods and Applications, 1990, Innis, M. et al., eds. Academic Press, Inc., New York).

Additionally, methods may be employed which result in the simultaneous identification of genes which encode the intracellular proteins interacting with PKB Kinase. These methods include, for example, probing expression libraries in a manner similar to the well known technique of antibody probing of λgt11 libraries, using labeled protein, or fusion protein, e.g., fused to a marker (e.g., and enzyme, fluor, luminescent protein, or dye). or an Ig-Fc domain.

One method which detects protein interactions in vivo, and which does not rely on the kinase activity of PKB Kinase, is the tyo-hybrid system, and is described in detail for illustration only and not by way of limitation. This system has been described ( U.S. Pat. No. 5,283,173 Chien et al., 1991, *Proc. Natl. Acad. Sci. USA*, 88:9578–9582) and is commercially available from Clontech (Palo Alto, Calif.). Briefly, utilizing such a system, plasmids are constructed that encode two hybrid proteins: one plasmid consists of nucleotides encoding the DNA-binding domain of a transcription activator protein fused to a PKB nucleotide sequence encoding PKB, or peptide or fusion protein, and the other plasmid consists of nucleotides encoding the transcription activator protein's activation domain fused to a cDNA encoding an unknown protein which has been recombined into this plasmid as a part of the cDNA library. The DNA-binding domain fusion plasmid and the cDNA library are transformed into a strain of the yeast *Saccharomyces cerevisiae* that contains a reporter gene (e.g., HBS or lacZ) whose regulatory region contain the transcription activator's binding site. Either hybrid protein alone cannot activate transcription of the reporter gene; the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, PKB or a peptide, or fusion protein derived therefrom may be used as the bait gene product. Total genomic or cDNA sequences are fused to the DNA encoding an activation domain. This library and a plasmid encoding a hybrid of a bait PKB gene product fused to the DNA-binding domain are cotransformed into a yeast reporter strain, and the resulting tranformants are screened for those that express the reporter gene. These colonies are purified and the library plasmids responsible for reporter gene expression are isolated. DNA sequencing is then used to identify the proteins encoded by the library plasmids.

A cDNA library of the cell line from which proteins that interact with bait cell cycle target gene product are to be detected can be made using methods routinely practiced in the art. According to the particular system described herein, for example, the cDNA fragments can be inserted into a vector such that they are translationally fused to the transcriptional activation domain of GAL4. This library can be co-transfected along with the bait cell cycle target gene-GAL4 fusion plasmid into a yeast strain which contains a lacZ gene driven by a promoter which contains GAL4 activation sequence. A cDNA encoded protein, fused to GAL4 transcriptional activation domain, that interacts with bait cycle target gene product will reconstitute an active GAL4 Protein and thereby drive expression of the HIS3 gene. Colonies which express HIS3 can be detected by their growth on petri dishes containing semi-solid agar based media lacking histidine. The cDNA can then be purified from these strains, and used to produce and isolate the bait cycle target gene-interacting protein using techniques routinely practiced in the art.

Whenever a protein is isolated using the two-hybrid assay, an independent assay to ascertain whether the protein has kinase activity is performed. Such assays are well known in the art, and an example is described by Stokoe, D., et al. (1997), *Science*, Vol. 277, pages 567–570.

PKB Kinase Encoding Nucleic Acid

A PKB kinase encoding nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell at a particular stage of development, having a desired genotype, phenotype (e.g., an oncogenically transformed cell or a cancerous cell), etc.

A nucleic acid comprising a nucleotide sequence coding for a polypeptide according to the present invention can include only coding sequence of PKB kinase coding sequence of PKB kinase and additional coding sequence (e.g., sequences coding for leader, secretory, targeting, enzymatic, fluorescent or other diagnostic peptides), coding sequence of PKB kinase and non-coding sequences, e.g., untranslated sequences at either a 5' or 3' end, or dispersed in the coding sequence, e.g., introns. A nucleic acid comprising a nucleotide sequence coding without interruption for a PKB kinase polypeptide means that the nucleotide sequence contains an amino acid coding sequence for a PKB kinase polypeptide, with no non-coding nucleotides interrupting or intervening in the coding sequence, e.g., absent intron(s). Such a nucleotide sequence can also be described as contiguous.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids which hybridize to a nucleic acid comprising a nucleotide sequence as set forth in FIG. 5 (SEQ ID NO: 1). A nucleotide sequence hybridizing to the latter sequence will have a complementary nucleic acid strand, or act as a template for one in the presence of a polymerase (ire., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIG. 5 (SEQ ID NO: 1). A nucleic acid capable of hybridizing to such sequence, preferably, possesses 50%, more preferably, 70% complementarity, between the sequences. The present invention particularly relates to DNA sequences which hybridize to the nucleotide sequence set forth in FIG. 5 (SEQ ID NO: 1) under stringent conditions. As used here, "stringent conditions" means any conditions in which hybridization will occur where there is at least about 95%, preferably 97%, nucleotide complementarity between the nucleic acids. Such conditions include, e.g., hybridization for Northern: 5×SSPE, 10×Denhardts solution, 100 µg/ml freshly denatured and sheared salmon sperm DNA, 50% formamide, 2% SDS at 42° C.; hybridization for cloning from cDNA library: 1×PAM, 0.1% SDS, 50% formamide at 42° C.

According to the present invention, a nucleic acid or polypeptide can comprise one or more differences in the nucleotide or amino acid sequence set forth in FIG. 5 (SEQ ID NO: 1). Changes or modifications to the nucleotide and/or amino acid sequence can be accomplished by any method available, including directed or random mutagenesis.

A nucleic acid coding for a PKB kinase according to the invention can comprise nucleotides which occur in a naturally-occurring PKB kinase gene e.g., naturally-occurring polymorphisms, normal or mutant alleles (nucleotide or amino acid), mutations. which are discovered in a natural population of mammals, such as humans, monkeys, pigs, mice, rats, or rabbits. By the term naturally-occurring, it is meant that the nucleic acid is obtained from a natural source, e.g., animal tissue and cells, body fluids, tissue culture cells, forensic samples. Naturally-occurring mutations to PKB kinase can include deletions (e.g., a truncated amino- or carboxy-terminus), substitutions, or additions of nucleotide sequence. These genes can be detected and isolated by nucleic acid hybridization according to methods which one skilled in the art would know. It is recognized that, in analogy to other oncogenes, naturally-occurring variants of PKB kinase include deletions, substitutions, and additions which produce pathological conditions in the host cell and organism.

A nucleotide sequence coding for a PKB kinase polypeptide of the invention can contain codons found in a naturally-occurring gene, transcript, or cDNA, for example, e.g., as set forth in FIG. 5 (SEQ ID NO: 1), or it can contain degenerate codons coding for the same amino acid sequences.

Another aspect of the present invention is a nucleotide sequence which is unique to PKB kinase. By a unique sequence to PKB kinase, it is meant a defined order of nucleotides which occurs in PKB kinase, e.g., in the nucleotide sequence of FIG. 5 (SEQ ID NO: 1), but rarely or infrequently in other nucleic acids, especially not in an animal nucleic acid, preferably mammal. such as human, rat, mouse, etc. Both sense and antisense nucleotide sequences are included. A unique nucleic acid according to the present invention can be determined routinely. A nucleic acid comprising a unique sequence of PKB kinase can be used as a hybridization probe to identify the presence of PKB kinase in a sample comprising a mixture of nucleic acids, e.g., on a Northern blot. Hybridization can be performed under stringent conditions to select nucleic acids having at least 95% identity (i.e., complementarity) to the probe, but less stringent conditions can also be used. A unique PKB kinase nucleotide sequence can also be fused in-frame, at either its 5' or 3' end. to various nucleotide sequences as mentioned throughout the patent, including coding sequences for other parts of PKB kinase, enzymes, GFP, etc, expression control sequences, etc.

Hybridization can be performed under different conditions, depending on the desired selectivity, e.g., as described in Sambrook et al., *Molecular Cloning*, 1989. For example, to specifically detect PKB kinase, an oligonucleotide can be hybridized to a target nucleic acid under conditions in which the oligonucleotide only hybridizes to PKB kinase, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%. Since a mutation in a PKB kinase gene can cause diseases or pathological conditions, e.g., cancer, benign tumors, an oligonucleotide according to the present invention can be used diagnostically. For example, a patient having symptoms of a cancer or other condition associated with the PKB kinase signaling pathway can be diagnosed with the disease by using an oligonucleotide according to the present invention, in polymerase chain reaction followed by DNA sequencing to identify whether the sequence is normal. In a preferred method, the present invention relates to a method of diagnosing a cancer comprising contacting a sample comprising a target nucleic acid with an oligonucleotide under conditions effective to permit hybridization between the target and oligonucleotide; detecting hybridization, wherein the oligonucleotide comprises a sequence of PKB kinase, preferably a unique sequence of PKB kinase; and determining the nucleotide sequence of the target nucleic acid to which the oligonucleotide is hybridized. The sequence can be determined according to various methods, including isolating the target nucleic acid, or a cDNA thereof, and determining its sequence according to a desired method.

DIAGNOSIS OF CELL GROWTH DISORDERS

A variety of methods can be employed for the diagnostic and prognostic evaluation of cell growth disorders, including cancer, and for the identification of subjects having a predisposition to such disorders.

Such methods may, for example, utilize reagents. such as the PKB kinase nucleotide sequences, and PKB kinase antibodies, as described above. Specifically, such reagents may be used, for example, for: (1) the detection of the presence of PKB kinase gene mutations, or the detection of either over- or under-expression of PKB kinase mRNA relative to the non cell growth disorder state; (2) the detection of either an over- or an under-abundance of PKB kinase gene product relative to the non-cell growth disorder state; and (3) the detection of perturbations or abnormalities in the signal transduction pathway mediated by PKB kinase.

The methods described herein may be performed, for example, by utilizing pre-packaged diagnostic kits comprising at least one specific PKB kinase nucleotide sequence or PKB kinase antibody reagent described herein, which may be conveniently used, e.g., in clinical settings, to diagnose patients exhibiting cell activation disorder abnormalities.

For the detection of PKB kinase, any nucleated cell can be used as a starting source for genomic nucleic acid. For the detection of PKB kinase expression, any cell type or tissue in which the PKB kinase is expressed may be utilized.

Nucleic acid-based detection techniques are described, below. Peptide detection techniques are also described below.

DETECTION OF PKB KINASE GENE AND TRANSCRIPTS

Mutations within the PKB kinase gene(s) can be detected by utilizing a number of techniques. Nucleic acid from any nucleated cell can be used as the starting point for such assay techniques, and may be isolated according to standard nucleic acid preparation procedures which are well known to those of skill in the art.

DNA may be used in hybridization or amplification assays of biological samples to detect abnormalities involving gene structure, including point mutations, insertions, deletions and chromosomal rearrangements. Such assays may include, but are not limited to, Southern analyses, single stranded conformational polymorphism analyses (SSCP), and PCR analyses.

Such diagnostic methods for the detection of PKB kinase specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described above, under conditions favorable for the specific annealing of these reagents to their complementary sequences within the PKB kinase. Preferably, the lengths of these nucleic acid reagents are at least 15 to 30 nucleotides. After incubation, all non-annealed nucleic acids are removed from the nucleic acid molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described above are easily removed. Detection of the remaining, annealed, labeled PKB kinase nucleic acid reagents is accomplished using standard techniques well known to those in the art. The PKB kinase gene sequences to which the nucleic acid reagents have annealed can be compared to the annealing pattern expected from a normal gene sequence in order to determine whether a gene mutation is present.

Alternative diagnostic methods for the detection of PKB kinase gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal copies of the PKB kinase gene in order to determine whether a gene mutation exists.

DETECTION OF THE PKB KINASE GENE PRODUCTS

Antibodies directed against wild type or mutant PKB kinase gene products or conserved variants or peptide fragments thereof, which are discussed, above, may also be used as cell growth disorder diagnostics and prognostics, as described herein. Such diagnostic methods, may be used to detect abnormalities in the level of PKB kinase gene expression, or abnormalities in the structure and/or temporal, tissue, cellular, or subcellular location of the PKB kinase, and may be performed in vivo or in vitro, such as, for example, on biopsy tissue.

The tissue or cell type to be analyzed will generally include those which are known, or suspected, to contain cells express the PKB kinase gene, such as, for example, neutrophil cells which have infiltrated an inflamed tissue. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a patient. The analysis of cells taken from culture may be a necessary step in the assessment of cells that could be used as part of a cell-based gene therapy technique or, alternatively, to test the effect of compounds on the expression of the PKB kinase gene.

For example, antibodies, or fragments of antibodies, such as those described above are useful in the present invention to quantitatively or qualitatively detect the presence of PKB kinase gene products or conserved variants or peptide fragments thereof. This can be accomplished, for example, by immunofluorescence techniques employing a fluorescently labeled antibody (see below) coupled with light microscopic, flow cytometric, or fluorimetric detection.

The antibodies (or fragments thereof) or fusion or conjugated proteins useful in the present invention may, additionally. be employed histologically, as in immunofluorescence, immunoelectron microscopy or non-immuno assays, for in situ detection of PKB kinase gene products or conserved variants or peptide fragments thereof In situ detection may be accomplished by removing a histological specimen from a patient, and applying thereto a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the PKB kinase gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for PKB kinase gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying PKB kinase gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled PKB kinase antibody or fusion protein. The solid phase support may then be washed with the buffer a second time to remove unbound antibody or fusion protein. The amount of bound label on solid support may then be detected by conventional means.

"Solid phase support or carrier" is intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of PKB kinase antibody or fusion protein may be determined according to well known methods. Those skilled in the art will be able to determine operative and optimal assay conditions for each determination by employing routine experimentation.

With respect to antibodies, one of the ways in which the antibody can be detectably labeled is by linking the same to an enzyme and use in an enzyme immunoassay (EIA) (Voller, "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler, 1981, Meth. Enzymol. 73:482–523; Maggio (ed.), 1980, Enzyme Immunoassay, CRC Press, Boca Raton, Fla.,; Ishikawa et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase. yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect PKB kinase through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and acquorin.

PHARMACEUTICAL PREPARATIONS

The compounds that are determined to affect PKB kinase gene expression or PKB kinase activity, or the interaction of PKB kinase with any of its binding partners including but not limited to PIP3 or PKB, can be administered to a patient at therapeutically effective doses to treat or ameliorate hematopoietic cell growth disorders, including cancer. A therapeutically effective dose refers to that amount of the compound sufficient to result in amelioration of symptoms of such disorders.

EFFECTIVE DOSE

Toxicity and therapeutic efficacy of such compounds can be determined by standard pharmaceutical procedures in cell cultures or experimental animals, e.g., for determining the, $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

The compounds may be formulated for parenteral administration by injection, e.g., by bolus injection or continuous infusion. Formulations for injection may be presented in unit dosage form, e.g., in ampoules or in multi-dose containers, with an added preservative.

The following examples are presented to illustrate the present invention and to assist one of ordinary skill in making and using the same. The examples are not intended in any way to otherwise limit the scope of the disclosure or the protection granted by Letters patent hereon.

EXAMPLE 1

Purification of PKB Kinase

The assay used to purify PKB kinase activities contained 1 µl of column fraction which was mixed with 5 µl of a mixture (put together 5 mins before use and stored on ice) of: 1) 3 µl of [$\gamma^{32}$P]-ATP 5 µCi; (1 µM final concentration in assay); 2) 1 µl of assay buffer (0.1 M KCl, 5 mM MgCl$_2$, 1 mM EGTA, 30 mM HEPES, pH 7.4, 30° C.; final concentrations in a 6 µl assay); 3) 0.5 µl of (EE)-PKB (final concentration 2.5 µM; the stock was in PBS containing 1 mM DTT, 1 mM EGTA and then mixed 1:1 (v/v) with glycerol; the kinase was purified from SF9 cells infected with clonal, recombinant bacullo-virus, the protein purified via its (EE)-tag and the eluting peptide removed by gel-filtration); 4) 0.5 µl of a lipid vesicle preparation containing phosphatidylserine, phosphatidylcholine, phosphatidylethanolamine with or without D-D-S/A-PtdIns(3,4,5)P$_3$ (final concentrations in the assay of 100, 100, 20 and 15 µM respectively, the vesicles were prepared by sonicating a dry film of the lipids into 25 mM HEPES (pH 7.4, 30° C.) and were stored at 4° C. for up to 3 days). The assays were run for 12 mins at 30° C., stopped by the addition of 400 µl of ice-cold 1% triton X100, 0.3 M NaCl, 10 mM EDTA, 1 mM sodium pyrophosphate, 10 mM p-glycerophosphate, 50 mM sodium flouride, 1 mM EGTA, 0.01% azide, 25 mM HEPES pH 7.4, 4° C. and then 30 µl of α(EE) beads (4 µl of packed beads per assay; protein G-sepharose covalently crosslinked to a saturating quantity of α(EE) monoclonal antibody). The tubes were mixed at 4° C. for 25 mins then washed once with the above stop buffer and the [$^{32}$P]-content of each tube was quantitated with a Geiger counter. Column fractions were diluted such that a maximum of 40–45% of the total [$\gamma^{32}$P]-ATP was consumed in any assay. HPLC-SEC was performed with a Biosilect column (VT 11.6 mls, BioRad). 35–45 μl samples were loaded, the flow was 40 μl min$^{-1}$, 80 μl fractions were collected. The SEC buffer contained 0.15 M NaCl, 20 mM HEPES pH 7.4 4° C., 0.5 mM EGTA 0.1 mM EDTA, 1% betaine, 0.03% Tween 20, 0.01% azide, 2 mM β-glycerophosphate, 1 mM DTT and pepstatin A, leupeptin, aprotinin and antipain (all 2 μgml$^{-1}$).

Figure 1C:
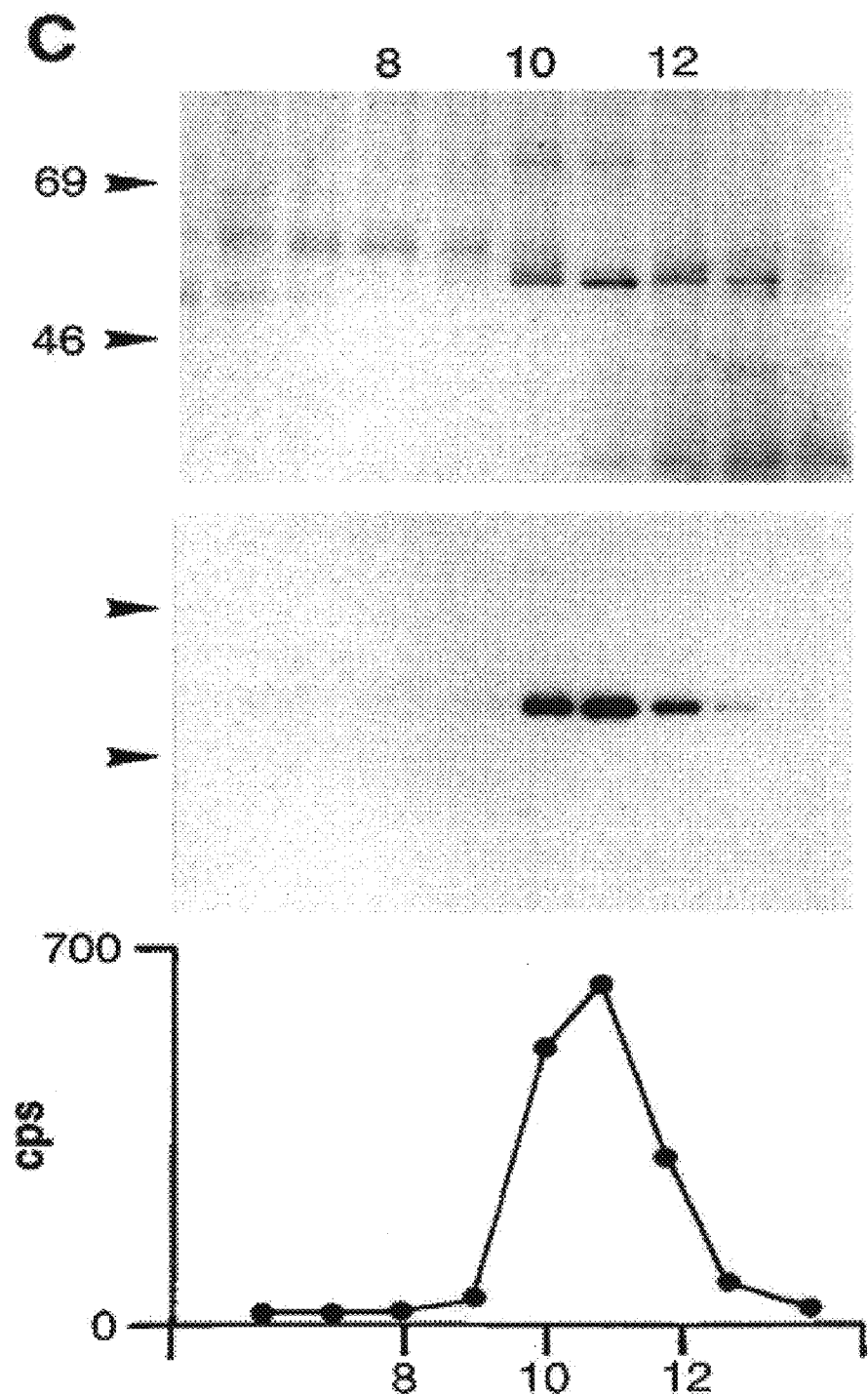

FIG. 1 shows that phosphatidylinositol(3,4,5)-trisphosphate ($^{32}$P$_1$-PtdIns(3,4,5)P$_3$ binding protein(s) co-purify with the PKB kinase activity and that ultimately four distinct forms of PKB kinase can be resolved from larger scale versions of similar partially-purified preparations. All four activities phosphorylate and activate (as judged by mylein basic protein (MBP) phosphorylation) PKB in the presence of the biological stereoisomers of PtdIns(3,4,5)P$_3$ or PtdIns(3,4)P$_2$ (e.g. (1-stearoyl, 2-arachidonyl) sn-phosphatidyl D-myoinositol(3,4,5)-trisphosphate: 'D-D-S/A-PtdIns(3,4,5)P$_3$'; See, FIG. 2A.

The results showed that the purified kinases were, like the partially purified activity, (a) inactive against PKB in the presence of the enantiomers of these lipids or PtdIns(4,5)P$_2$; (b) active at lower concentrations of stearoylarachidonyl than dipalmitoyl versions of these lipids and (c) equally effectively activated by D-D-S/A-PtdIns(3,4,5)P$_3$ and its diastereoisomer only differing in the arrangement of the chiral centre in the glycerol backbone (i.e. D-L-S/A-PtdIns (3,4,5)P$_3$) suggesting that although recognition/interaction is dependent on the nature of the fatty acids it is not dictated by their precise stereochemistry with respect to the water soluble headgroup; FIG. 2B.

Under the same assay conditions used for the PKB phosphorylation studies, we investigated the association of both the PKB kinases and PKB itself (FIG. 2C) with the lipid vesicles in these assays. To assay association of PKB and PKB kinases with lipid vesicles and the effects of different lipids on the phosphorylation of PKB, the lipid vesicles were prepared by: sonicating dry lipid films into 0.2 M sucose; 20 mM KCl; 20 mM HEPES, pH 7.4 30° C.; 0.01% azide (to give 200 μM phosphatidylcholine, 150 μM phosphatidylserine, 20 μM phosphatidylethanolamine, 10 μM spingomylin plus the indicated concentrations of inositol lipids final in the assay. These were mixed with the relevant kinases in an assay buffer containing 1 mgml$^{-1}$ BSA; 0.12 M NaCl; 1 mM EGTA; 0.2 mM calcuim; 1.5 mM MgCl$_2$; 1 mM DTT; 0.01% azide; 5 mM KCl; 20 mM HEPES, pH 7.4, 30° C. (approx. 50 nM free calcium, all final concentrations in assay) with or without [$\gamma^{32}$P]-ATP (1 μM final concentration) and (EE)-PKB (2.5 μM final concentration). If the assays were to estimate associated of the kinases with the lipid vesicles then after 4 mins at 30° C. the assays were centrifuged (airfuge (Beckman) maximum speed for 30 mins). Aliquots of the supernatents were removed for assays or immunoblotting. The pellets were rinsed rapidly with assay buffer, recentrifuged and dissolved in SDS-sample buffer. Phosphorylation of PKB(s) was quantitated as described herein.

The PKB kinases associated with the lipid vesicles containing very low molar percentages of the PtdIns(3,4,5)P$_3$ stereoisomers (0.003% for D-D-S/A PtdIns(3,4,5)P$_3$) and D-D-P/P-PtdIns(3,4)P$_2$ but not PtdIns(4,5)P$_2$ or L-L-P/P-PtdIns(3,4)P$_2$. This is consistent with the observations that the PKB kinases(s) can bind [$^{32}$P]-PtdIns(3,4,5)P$_3$ and that phosphorylation of a water-soluble, 30-mer peptide, based on the sequence of PKB around Thr308, was dramatically inhibited by PtdIns(3,4,5)P$_3$ or PtdIns(3,4)P$_2$ (not shown).

Figure 2C:
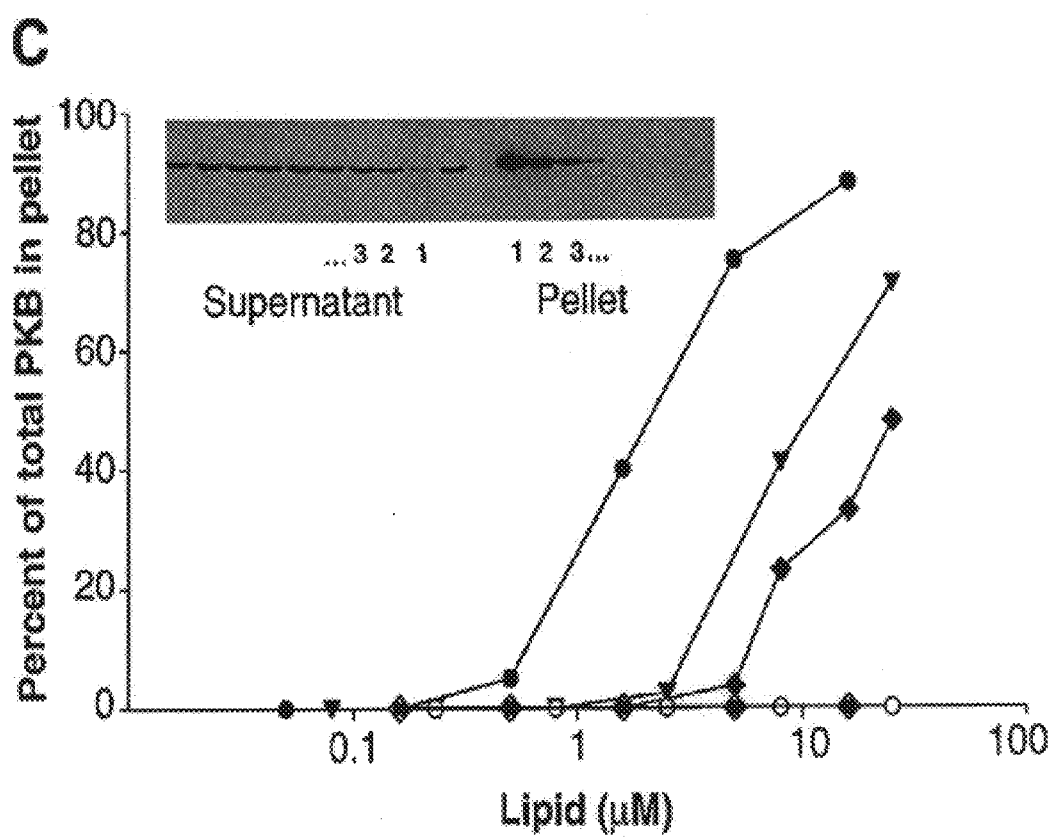

Under the same assay conditions PKB could also be shown to associate with the lipid vesicles (FIG. 2C). However, substantially higher concentrations of 3-phosphorylated lipids were required to detect translocation and further it showed different specificity for binding 3-phosphorylated lipids to that of the PKB kinases, but one that was very similar to that of the phosphorylation of PKB (compare FIGS. 2B and C). This implies several things; 1) that lipid binding properties of the two kinases are quite distinct, 2) that the specificity of the phosphorylation is largely dictated by the recruitment of PKB (i.e. the affinity and specificity of PKB's PH domain), 3) that only a relatively small proportion of the PKB is probably associated with the vesicles at concentrations of active lipids that have caused the majority of PKB kinase to associate and hence 4) that the relatively biggest effects of the translocation of PKB kinase on the phosphorylation of PKB will be experienced at very low concentrations of PtdIns(3,4,5)P$_3$, while at higher levels, the translocation of PKB becomes the major factor.

A preparation of PKB kinase A was Western blotted onto nitrocellulose and trypsinised in situ. The liberated peptides were subjected to analysis by N-terminal sequencing and mass spectrometry. See, L. R. Stephens et al, *Cell* 89, 105–114 (1997). Four peptides were defined and used to search the data bases; a family of human EST sequences were identified (TIGR: THC193570). Combined use of the peptide sequences (to fix the reading frame) and information from further sequencing of the EST clones and of cDNAs isolated from a human U937 cell cDNA library defines a cDNA with a minimum potential open reading frame containing all four peptides (allowing for species differences) and encoding a protein with a predicted molecular mass of 55 kd (FIG. 3). This predicted protein contains an NH$_2$-terminal protein kinase domain and a COOH-terminal PH domain (FIG. 3).

Human and mouse EST sequences relating to the PKB kinase gene can be found in the TIGR database (THC: 193570). Further cDNAs encoding PKB kinases were identified by screening a human U937 cell oligo dT-primed library (in λZAPII; Stratagene) and a rat brain oligo dT/random primed library (in UniZAPXR; Stratagene) with a [$^{32}$P]-labelled 0.3 kb EcoRI-HindIII fragment derived from IMAGE clone 526583. Positive plaques were identified, purified and the cDNAs excised as pBluescript®-based plasmids. DNA sequencing was performed on an ABI automatic sequencer by the Babraham Institute Microchemical Facility.

EXAMPLE 2

Identification of PKB Kinase cDNA

Using genomic sequence information in the data bases we were able to define a precise chromosomal localization (human chromosome 16P13.3; (See, T. C. Bunn et al., *Genome Research* 6, 525–537 (1996).)) and some, but not all, intron/exon boundaries of the PKB kinase. It is clear from this information and from sequencing a number of cDNAs that this locus gives rise to a complex pattern of alternatively spliced transcripts. One transcript identified from our U937 cell library is precisely equivalent to the ORF defined in FIG. 3 except that it is missing the exon encoding the substrate recognition motif of the protein kinase domain (residues: 188–213; our peptide sequence data shows unambiguously that our purified enzyme contained this motif, FIG. 3). We have made use of this cDNA to generate a kinase-compromised version of the PKB kinase (see below).

We have identified further cDNA clones from a rat brain cDNA library which clearly arose from the equivalent gene locus but which extend the potential ORF shown in FIG. 3 to encode a protein of approximately 65kd. It seems likely that alternative splicing or start codon usage will be responsible for generating more than one isoform of PKB kinase from this gene locus (NOTE: the most N-terminal PKB kinase A peptide shown in FIG. 3 diverges from the predicted ORF shown, perhaps indicating that truncated forms of this enzyme may be produced by alternative splicing). Further database searching also identifies a close homologue of unknown function in Drosophila (Embl: Y07908). See, K. Salim et al., *EMBO J.* 15, 6241–6250 (1996).

EXAMPLE 3

Expression of PKB Kinase

We have constructed mammalian expression vectors encoding N-terminally EE-tagged forms of the 55 kd PKB kinase and its 'kinase-compromised' splice variant. The ORF defined in FIG. 3 was placed in frame with an N-terminal EE-tag in the pCMV3 transient expression vector (See, L. R. Stephens et al, *Cell* 89, 105–114 (1997)) by using standard PCR-based cloning strategies. A version was also constructed using a cDNA missing the nucleotides coding for residues 188–213 (this was made using IMAGE clones 510982 and 526583: referred to in the text as the 'kinase-compromised splice varient'). All constructs were verified by sequencing. These proteins were expressed in, and purified from cos-7 cells (See, L. R. Stephens et al, *Cell* 89, 105–114 (1997), see, FIG. 4.). The protein with the intact protein kinase domain phosphorylated PKB in a PtdIns(3,4,5)P$_3$-sensitive manner indicating that this activity resided in the ORF defined in FIG. 3.

Briefly, proteins were purified via their (EE)-tags (myc antibodies were used as controls) and aliquots were Western blotted. PVDF filters, probed with an α(EE) monoclonal antibody (detection by ECL; right hand upper panel) were then stained with Coomassie blue (left hand upper panel; data shown are for (EE)-II only; similar results were obtained with (EE)-I). Aliquots were assayed for PKB kinase activity in the presence of lipid vesicles either with or without D-D-S/A-PtdIns(3,4,5)P$_3$ and [γ$^{32}$P]-ATP (300 nM; 3 μM and 1 μM final concentrations, respectively). A photograph of an autoradiogram is shown displaying [$^{32}$P] in PKB.

EXAMPLE 4

Identification and Uses of PKB Kinase Inhibitors

PKB is a key enzyme in the PIP3 pathway, and is involved in regulating cell growth. It has been implicated in certain human cancers; for instance, it is known to be amplified in a percentage of ovarian carcinomas, breast carcinomas, and pancreatic carcinomas. See, Bellacosa, A. et al. (1995) Int. J. Cancer 64, pages 280–285, and Cheng, J. Q. et al. (1996) Proc. Natl. Acad. Sci. U.S.A. vol. 93, 3636–3641. The amplification of the enzyme affords tumor cells a mechanism to circumvent apoptosis. Thus, it will be appreciated that drugs that inhibit PKB activity will be beneficial for the treatment of diseases involving unwanted cell growth, including cancer. One way to achieve this end is to develop assays that measure the effect of compounds on PKB kinase activity.

The identification of PKB kinase inhibitors can be achieved by assaying for compounds that inhibit PIP3 activation of PKB kinase activity. This would be done by measuring PKB phosphorylation in the presence and absence of a compound. The assay can be carried out as described above, or by Stokoe, D., et al (1997) Science, vol. 277, pages 567–570. For instance, using the assay described in Example 3, terminally EE-tagged forms of the 55 kd PKB kinase would be incubated with PIP3, an ATP regenerating system, preferably consisting of 5 mM MgCl2, 2 mM ATP, 10 mM creatine phosphate, creatine kinase (50 ug/ml), 1% NP-40, and PKB, or another suitable substrate. After an appropriate period of time, PKB can be immunoprecipitated and the amount of phosphorlyation determined.

The present invention is not to be limited in scope by the specific embodiments described herein. which are intended as single illustrations of individual aspects of the invention, and functionally equivalent methods and components are within the scope of the invention. Indeed, various modifications of the invention, in addition to those shown and described herein w ill become apparent to those skilled in the art from the foregoing description and accompanying drawings. Such modifications are intended to fall within the scope of the appended claims.

We claim:

1. An isolated nucleic acid molecule comprising a nucleotide sequence which encodes PKB kinase having the amino acid sequence shown in SEQ ID No. 2.

2. An isolated nucleotide sequence encoding a chimeric protein comprising the nucleotide sequence of claim 1 fused to a second nucleotide sequence that encodes a heterologous polypeptide.

3. An isolated nucleic acid molecule comprising a nucleotide sequence shown in SEQ ID No. 1.

4. A nucleotide vector comprising the nucleotide sequence of claim 1.

5. An expression vector comprising the nucleotide sequence of claim 1 in operative association with a nucleotide regulatory sequence that controls expression of the nucleotide sequence in the host cell.

6. A host cell that has been genetically engineered to comprise the nucleotide sequence of claim 1.

7. A host cell that has been genetically engineered to comprise the nucleotide sequence of claim 1 in operative association with a nucleotide regulatory sequence that controls expression of the nucleotide sequence in the host cell.

8. An isolated PKB kinase comprising SEQ ID No. 2.

9. A method for screening compounds useful for the treatment of cell growth disorders, comprising the steps of:

combining in solution a compound, activated PKB kinase wherein said PKB kinase has the amino acid sequence of SEQ ID No. 2, a substrate for PKB kinase, an ATP regenerating system, and a PKB activating agent in the presence of phospholipid vesicles, and;

assaying the transfer of phosphate from ATP to the PKB kinase substrate in the presence or absence of said compound.

10. The method of claim 9 wherein said PKB activating agent is PIP3 and said PKB kinase substrate is PKB.

11. The method of claim 9 wherein said PKB kinase is encoded by a nucleotide sequence that:

hybridizes under stringent conditions to the nucleotide sequence of SEQ ID No:1 and encodes the amino acid sequence of SEQ ID No. 2.

12. A method for activating PKB kinase wherein said PKB kinase has the amino acid sequence of SEQ ID No:2 comprising incubating in solution said PKB kinase with PIP3 in the presence of phospholipid vesicles.

13. The method of claim 12 wherein said PKB kinase is encoded by a nucleotide sequence that:

hybridizes under stringent conditions to the nucleotide sequence of SEQ ID No:1 and encodes the amino acid sequence of SEQ ID No. 2.

* * * * *

SEQUENCE LISTING

```
<160> NUMBER OF SEQ ID NOS:  2

<210> SEQ ID NO 1
<211> LENGTH: 1864
<212> TYPE: DNA
<213> ORGANISM: PKB Kinase
<220> FEATURE:
<221> NAME/KEY: CDS
<222> LOCATION: Complement((52)..(1722))

<400> SEQUENCE: 1
cgcggagcag cgcaacgctg cggggggaggc gcccgcgccg actcggggct c atg gcc        57
                                                         Met Ala
                                                          1
```

-continued

| | | |
|---|---|---|
| agg acc acc agc cag ctg tat gac gct gtg ccc att cag tcc agt gtg<br>Arg Thr Thr Ser Gln Leu Tyr Asp Ala Val Pro Ile Gln Ser Ser Val<br>　　　5　　　　　　　　　10　　　　　　　　　15 | | 105 |
| gtg cta tgt tcc tgc cca tcc cca tca atg gtg agg tcc cag act gag<br>Val Leu Cys Ser Cys Pro Ser Pro Ser Met Val Arg Ser Gln Thr Glu<br>　　20　　　　　　　　　25　　　　　　　　　30 | | 153 |
| tcc agc acg ccc cct ggc att cct ggt ggc agc agg cag ggc ccc gcc<br>Ser Ser Thr Pro Pro Gly Ile Pro Gly Gly Ser Arg Gln Gly Pro Ala<br>35　　　　　　　　　40　　　　　　　　　45　　　　　　　　　50 | | 201 |
| atg gac ggc act gca gcc gag cct cgg ccc ggc gcc ggc tcc ctg cag<br>Met Asp Gly Thr Ala Ala Glu Pro Arg Pro Gly Ala Gly Ser Leu Gln<br>　　　　　　　　　55　　　　　　　　　60　　　　　　　　　65 | | 249 |
| cat gcc cag cct ccg ccg cag cct cgg aag aag cgg cct gag gac ttc<br>His Ala Gln Pro Pro Pro Gln Pro Arg Lys Lys Arg Pro Glu Asp Phe<br>　　　　　　70　　　　　　　　　75　　　　　　　　　80 | | 297 |
| aag ttt ggg aaa atc ctt ggg gaa ggc tct ttt tcc acg gtt gtc ctg<br>Lys Phe Gly Lys Ile Leu Gly Glu Gly Ser Phe Ser Thr Val Val Leu<br>　　　　　85　　　　　　　　　90　　　　　　　　　95 | | 345 |
| gct cga gaa ctg gca acc tcc aga gaa tat gcg att aaa att ctg gag<br>Ala Arg Glu Leu Ala Thr Ser Arg Glu Tyr Ala Ile Lys Ile Leu Glu<br>　　　100　　　　　　　　　105　　　　　　　　　110 | | 393 |
| aag cga cat atc ata aaa gag aac aag gtc ccc tat gta acc aga gag<br>Lys Arg His Ile Ile Lys Glu Asn Lys Val Pro Tyr Val Thr Arg Glu<br>115　　　　　　　　　120　　　　　　　　　125　　　　　　　　　130 | | 441 |
| cgg gat gtc atg tcg cgc ctg gat cac ccc ttc ttt gtt aag ctt tac<br>Arg Asp Val Met Ser Arg Leu Asp His Pro Phe Phe Val Lys Leu Tyr<br>　　　　　　　　　135　　　　　　　　　140　　　　　　　　　145 | | 489 |
| ttc aca ttt cag gac gac gag aag ctg tat ttc ggc ctt agt tat gcc<br>Phe Thr Phe Gln Asp Asp Glu Lys Leu Tyr Phe Gly Leu Ser Tyr Ala<br>　　　　　　150　　　　　　　　　155　　　　　　　　　160 | | 537 |
| aaa aat gga gaa cta ctt aaa tat att cgc aaa atc ggt tca ttc gat<br>Lys Asn Gly Glu Leu Leu Lys Tyr Ile Arg Lys Ile Gly Ser Phe Asp<br>　　　　　165　　　　　　　　　170　　　　　　　　　175 | | 585 |
| gag acc tgt acc cga ttt tac acg gct gag att gtg tct gct tta gag<br>Glu Thr Cys Thr Arg Phe Tyr Thr Ala Glu Ile Val Ser Ala Leu Glu<br>　　　180　　　　　　　　　185　　　　　　　　　190 | | 633 |
| tac ttg cac ggc aag ggc atc att cac agg gac ctt aaa ccg gaa aac<br>Tyr Leu His Gly Lys Gly Ile Ile His Arg Asp Leu Lys Pro Glu Asn<br>195　　　　　　　　　200　　　　　　　　　205　　　　　　　　　210 | | 681 |
| att ttg tta aat gaa gat atg cac atc cag atc aca gat ttt gga aca<br>Ile Leu Leu Asn Glu Asp Met His Ile Gln Ile Thr Asp Phe Gly Thr<br>　　　　　　　　　215　　　　　　　　　220　　　　　　　　　225 | | 729 |
| gca aaa gtc tta tcc cca gag agc aaa caa gcc agg gcc aac tca ttc<br>Ala Lys Val Leu Ser Pro Glu Ser Lys Gln Ala Arg Ala Asn Ser Phe<br>　　　　　　230　　　　　　　　　235　　　　　　　　　240 | | 777 |
| gtg gga aca gcg cag tac gtt tct cca gag ctg ctc acg gag aag tcc<br>Val Gly Thr Ala Gln Tyr Val Ser Pro Glu Leu Leu Thr Glu Lys Ser<br>　　　　　245　　　　　　　　　250　　　　　　　　　255 | | 825 |
| gcc tgt aag agt tca gac ctt tgg gct ctt gga tgc ata ata tac cag<br>Ala Cys Lys Ser Ser Asp Leu Trp Ala Leu Gly Cys Ile Ile Tyr Gln<br>　　　260　　　　　　　　　265　　　　　　　　　270 | | 873 |
| ctt gtg gca gga ctc cca cca ttc cga gct gga aac gag tat ctt ata<br>Leu Val Ala Gly Leu Pro Pro Phe Arg Ala Gly Asn Glu Tyr Leu Ile<br>275　　　　　　　　　280　　　　　　　　　285　　　　　　　　　290 | | 921 |
| ttt cag aag atc att aag ttg gaa tat gac ttt cca gaa aaa ttc ttc<br>Phe Gln Lys Ile Ile Lys Leu Glu Tyr Asp Phe Pro Glu Lys Phe Phe<br>　　　　　　　　　295　　　　　　　　　300　　　　　　　　　305 | | 969 |
| cct aag gca aga gac ctc gtg gag aaa ctt ttg gtt tta gat gcc aca<br>Pro Lys Ala Arg Asp Leu Val Glu Lys Leu Leu Val Leu Asp Ala Thr<br>　　　　　　310　　　　　　　　　315　　　　　　　　　320 | | 1017 |

-continued

```
aag cgg tta ggc tgt gag gaa atg gaa gga tac gga cct ctt aaa gca      1065
Lys Arg Leu Gly Cys Glu Glu Met Glu Gly Tyr Gly Pro Leu Lys Ala
        325                 330                 335 cac ccg ttc ttc gag tcc gtc acg tgg gag aac ctg cac cag cag acg      1113
His Pro Phe Phe Glu Ser Val Thr Trp Glu Asn Leu His Gln Gln Thr
    340                 345                 350 cct ccg aag ctc acc gct tac ctg ccg gct atg tcg gaa gac gac gag      1161
Pro Pro Lys Leu Thr Ala Tyr Leu Pro Ala Met Ser Glu Asp Asp Glu
355                 360                 365                 370 gac tgc tat ggc aat tat gac aat ctc ctg agc cag ttt ggc tgc atg      1209
Asp Cys Tyr Gly Asn Tyr Asp Asn Leu Leu Ser Gln Phe Gly Cys Met
                375                 380                 385 cag gtg tct tcg tcc tcc tcc tca cac tcc ctg tca gcc tcc gac acg      1257
Gln Val Ser Ser Ser Ser Ser His Ser Leu Ser Ala Ser Asp Thr
            390                 395                 400 ggc ctg ccc cag agg tca ggc agc aac ata gag cag tac att cac gat      1305
Gly Leu Pro Gln Arg Ser Gly Ser Asn Ile Glu Gln Tyr Ile His Asp
        405                 410                 415 ctg gac tcg aac tcc ttt gaa ctg gac tta cag ttt tcc gaa gat gag      1353
Leu Asp Ser Asn Ser Phe Glu Leu Asp Leu Gln Phe Ser Glu Asp Glu
    420                 425                 430 aag agg ttg ttg ttg gag aag cag gct ggc gga aac cct tgg cac cag      1401
Lys Arg Leu Leu Leu Glu Lys Gln Ala Gly Gly Asn Pro Trp His Gln
435                 440                 445                 450 ttt gta gaa aat aat tta ata cta aag atg ggc cca gtg gat aag cgg      1449
Phe Val Glu Asn Asn Leu Ile Leu Lys Met Gly Pro Val Asp Lys Arg
                455                 460                 465 aag ggt tta ttt gca aga cga cga cag ctg ttg ctc aca gaa gga cca      1497
Lys Gly Leu Phe Ala Arg Arg Arg Gln Leu Leu Leu Thr Glu Gly Pro
            470                 475                 480 cat tta tat tat gtg gat cct gtc aac aaa gtt ctg aaa ggt gaa att      1545
His Leu Tyr Tyr Val Asp Pro Val Asn Lys Val Leu Lys Gly Glu Ile
        485                 490                 495 cct tgg tca caa gaa ctt cga cca gag gcc aag aat ttt aaa act ttc      1593
Pro Trp Ser Gln Glu Leu Arg Pro Glu Ala Lys Asn Phe Lys Thr Phe
    500                 505                 510 ttt gtc cac acg cct aac agg acg tat tat ctg atg gac ccc agc ggg      1641
Phe Val His Thr Pro Asn Arg Thr Tyr Tyr Leu Met Asp Pro Ser Gly
515                 520                 525                 530 aac gca cac aag tgg tgc agg aag atc cag gag gtt tgg agg cag cga      1689
Asn Ala His Lys Trp Cys Arg Lys Ile Gln Glu Val Trp Arg Gln Arg
                535                 540                 545 tac cag agc cac ccg gac gcc gct gtg cag tga cggygtgcgg ccgggctgcc   1742
Tyr Gln Ser His Pro Asp Ala Ala Val Gln
            550                 555 cttcgctgcc aggacacctg ccccaacgcg gcttggccgc catccgggac gcttccagac   1802
cacctgccag ccatcacaag gggaacgcag aggcggaaac cttgcagcat ttttatttaa   1862
aa                                                                  1864

<210> SEQ ID NO 2
<211> LENGTH: 556
<212> TYPE: PRT
<213> ORGANISM: PKB Kinase

<400> SEQUENCE: 2

Met Ala Arg Thr Thr Ser Gln Leu Tyr Asp Ala Val Pro Ile Gln Ser
 1               5                  10                  15

Ser Val Val Leu Cys Ser Cys Pro Ser Pro Ser Met Val Arg Ser Gln
```

-continued

```
                 20                  25                  30
Thr Glu Ser Ser Thr Pro Pro Gly Ile Pro Gly Gly Ser Arg Gln Gly
             35                  40                  45
Pro Ala Met Asp Gly Thr Ala Ala Glu Pro Arg Pro Gly Ala Gly Ser
 50                  55                  60
Leu Gln His Ala Gln Pro Pro Gln Pro Arg Lys Lys Arg Pro Glu
 65                  70                  75                  80
Asp Phe Lys Phe Gly Lys Ile Leu Gly Glu Gly Ser Phe Ser Thr Val
                 85                  90                  95
Val Leu Ala Arg Glu Leu Ala Thr Ser Arg Glu Tyr Ala Ile Lys Ile
             100                 105                 110
Leu Glu Lys Arg His Ile Ile Lys Glu Asn Lys Val Pro Tyr Val Thr
             115                 120                 125
Arg Glu Arg Asp Val Met Ser Arg Leu Asp His Pro Phe Phe Val Lys
             130                 135                 140
Leu Tyr Phe Thr Phe Gln Asp Asp Glu Lys Leu Tyr Phe Gly Leu Ser
 145                 150                 155                 160
Tyr Ala Lys Asn Gly Glu Leu Leu Lys Tyr Ile Arg Lys Ile Gly Ser
             165                 170                 175
Phe Asp Glu Thr Cys Thr Arg Phe Tyr Thr Ala Glu Ile Val Ser Ala
             180                 185                 190
Leu Glu Tyr Leu His Gly Lys Gly Ile Ile His Arg Asp Leu Lys Pro
             195                 200                 205
Glu Asn Ile Leu Leu Asn Glu Asp Met His Ile Gln Ile Thr Asp Phe
             210                 215                 220
Gly Thr Ala Lys Val Leu Ser Pro Glu Ser Lys Gln Ala Arg Ala Asn
 225                 230                 235                 240
Ser Phe Val Gly Thr Ala Gln Tyr Val Ser Pro Glu Leu Leu Thr Glu
             245                 250                 255
Lys Ser Ala Cys Lys Ser Ser Asp Leu Trp Ala Leu Gly Cys Ile Ile
             260                 265                 270
Tyr Gln Leu Val Ala Gly Leu Pro Pro Phe Arg Ala Gly Asn Glu Tyr
             275                 280                 285
Leu Ile Phe Gln Lys Ile Ile Lys Leu Glu Tyr Asp Phe Pro Glu Lys
             290                 295                 300
Phe Phe Pro Lys Ala Arg Asp Leu Val Glu Lys Leu Leu Val Leu Asp
 305                 310                 315                 320
Ala Thr Lys Arg Leu Gly Cys Glu Glu Met Glu Gly Tyr Gly Pro Leu
             325                 330                 335
Lys Ala His Pro Phe Phe Glu Ser Val Thr Trp Glu Asn Leu His Gln
             340                 345                 350
Gln Thr Pro Pro Lys Leu Thr Ala Tyr Leu Pro Ala Met Ser Glu Asp
             355                 360                 365
Asp Glu Asp Cys Tyr Gly Asn Tyr Asp Asn Leu Leu Ser Gln Phe Gly
             370                 375                 380
Cys Met Gln Val Ser Ser Ser Ser Ser His Ser Leu Ser Ala Ser
 385                 390                 395                 400
Asp Thr Gly Leu Pro Gln Arg Ser Gly Ser Asn Ile Glu Gln Tyr Ile
             405                 410                 415
His Asp Leu Asp Ser Asn Ser Phe Glu Leu Asp Leu Gln Phe Ser Glu
             420                 425                 430
Asp Glu Lys Arg Leu Leu Leu Glu Lys Gln Ala Gly Gly Asn Pro Trp
             435                 440                 445
```

```
His Gln Phe Val Glu Asn Asn Leu Ile Leu Lys Met Gly Pro Val Asp
    450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
        515                 520                 525

Ser Gly Asn Ala His Lys Trp Cys Arg Lys Ile Gln Glu Val Trp Arg
    530                 535                 540

Gln Arg Tyr Gln Ser His Pro Asp Ala Ala Val Gln
545                 550                 555
```